(12) United States Patent
Bagala, Sr.

(10) Patent No.: US 8,088,212 B2
(45) Date of Patent: Jan. 3, 2012

(54) SPARKLE EFFECT OF UNIQUE PARTICLE SIZE DISTRIBUTION

(75) Inventor: Frank Bagala, Sr., Peekskill, NY (US)

(73) Assignee: BASF Corporation, Florham Park, NJ (US)

(*) Notice: Subject to any disclaimer, the term of this patent is extended or adjusted under 35 U.S.C. 154(b) by 685 days.

(21) Appl. No.: 11/277,897

(22) Filed: Mar. 29, 2006

(65) Prior Publication Data

US 2006/0223910 A1 Oct. 5, 2006

Related U.S. Application Data

(60) Provisional application No. 60/667,276, filed on Apr. 1, 2005.

(51) Int. Cl.
*C09C 1/00* (2006.01)
*C09C 1/36* (2006.01)

(52) U.S. Cl. ........................................ 106/415; 106/436

(58) Field of Classification Search .................. 106/31.6, 106/401, 403, 415, 417, 436; 424/63; 428/403, 428/404
See application file for complete search history.

(56) References Cited

U.S. PATENT DOCUMENTS

| | | | |
|---|---|---|---|
| 3,087,828 A | 4/1963 | Linton | |
| 3,087,829 A | 4/1963 | Linton | |
| 3,123,485 A | 3/1964 | Miller et al. | |
| 3,219,734 A | 11/1965 | Mattin | |
| 3,331,699 A | 7/1967 | Marshall et al. | |
| 3,616,100 A | 10/1971 | Morita | |
| 4,038,099 A | 7/1977 | DeLuca et al. | |
| 4,552,593 A | 11/1985 | Ostertag | |
| 4,735,869 A | 4/1988 | Morita | |
| 5,156,889 A | 10/1992 | DeLuca, Jr. | |
| 5,423,912 A | 6/1995 | Sullivan et al. | |
| 5,433,779 A | 7/1995 | DeLuca, Jr. | |
| 5,436,077 A | 7/1995 | Matsuba et al. | |
| 5,753,371 A * | 5/1998 | Sullivan et al. | 428/406 |
| 5,759,255 A | 6/1998 | Venturini et al. | |
| 6,045,914 A | 4/2000 | Sullivan et al. | |
| 6,132,873 A | 10/2000 | Dietz et al. | |
| 6,464,769 B2 * | 10/2002 | Chattopadhyay et al. | 106/403 |
| 6,702,885 B2 * | 3/2004 | Schoen et al. | 106/31.9 |
| 2002/0119302 A1 * | 8/2002 | Fritz | 428/325 |
| 2003/0178734 A1 * | 9/2003 | Josephy et al. | 264/81 |
| 2004/0123778 A1 | 7/2004 | Bagala, Sr. | |
| 2004/0134385 A1 * | 7/2004 | Anselmann et al. | 106/415 |
| 2004/0170838 A1 * | 9/2004 | Ambrosius et al. | 428/406 |
| 2004/0258640 A1 * | 12/2004 | Simon | 424/63 |
| 2005/0118122 A1 * | 6/2005 | Simon et al. | 424/63 |

FOREIGN PATENT DOCUMENTS

| | | |
|---|---|---|
| JP | 2002-155240 | 5/2002 |
| JP | 2002-155241 | 5/2002 |
| JP | 2002-155242 | 5/2002 |
| JP | 2002-155243 | 5/2002 |
| JP | 2002155240 * | 5/2002 |

OTHER PUBLICATIONS

Dr. R. Ruger et al.: "Cosmetic Formulations Containing Special Effect Pigments", Research Disclosure, Mason Publications, Hampshire, GB, vol. 471, No. 1, Jul. 2003.

* cited by examiner

*Primary Examiner* — Shuangyi Abu Ali
(74) *Attorney, Agent, or Firm* — Bernard Lau

(57) ABSTRACT

An effect pigment formed from a synthetic platelet substrate such as glass flake has improved sparkle by reducing the amount of substrate particles having a size of less than 9 microns and greater than 85 microns.

The present effect pigment is useful in cosmetics, personal care products, and industrial applications such as automotive paints.

20 Claims, No Drawings

SPARKLE EFFECT OF UNIQUE PARTICLE SIZE DISTRIBUTION

This patent application claims the benefit of pending Ser. No. 60/667276 filed Apr. 1, 2005 incorporated herein by reference in its entirety.

FIELD

The invention is directed to improvements in the optical properties of synthetic effect pigments by altering the size distribution of the substrates of the effect pigments.

BACKGROUND

Imparting a pearlescent luster, metallic luster and/or multi-color effects approaching iridescent can be achieved using a nacreous or pearlescent pigment which comprises a metal oxide-coated platelet. These pigments were first described in U.S. Pat. Nos. 3,087,828 and 3,087,829, and a description of their properties can be found in the Pigment Handbook, Vol. I, Second Edition, pp. 829-858, John Wiley & Sons, N.Y. 1988.

The oxide coating is in the form of a thin film deposited on the surfaces of the platelet. The oxide in most wide spread use at present is titanium dioxide. The next most prevalent is iron oxide while other usable oxides include tin, chromium and zirconium oxides as well as mixtures or combinations of oxides.

The coating of the metal oxide on the platelet must be smooth and uniform in order to achieve the optimum pearlescent appearance. If an irregular surface is formed, light scattering occurs, and the coated platelet will no longer function as a pearlescent pigment. The metal oxide coating must also adhere strongly to the platelet or else the coating will be separated during processing, resulting in considerable breakage and loss of luster.

During the preparation of these coatings on the platelets, particles which are not attached to the platelet may form. These small particles cause light scattering and impart opacity to the pigment. If too many small particles are present, the pearlescent appearance may be reduced or lost. The addition of these metal oxide coatings to a platelet so that the luster, color and color homogeneity are maintained can be a difficult process, and to date, the only platy substrate which has achieved any significant use in commerce is mica.

A wide variety of other platy materials have been proposed for use as a substrate for forming these pearlescent pigments. These include non-soluble inorganic materials such as glass, enamel, china clay, porcelain, or other silicaceous substances, metal objects and surfaces of organic polymer materials such as polycarbonate. See, e.g., U.S. Pat. Nos. 3,123,485; 3,219,734; 3,616,100; 3,444,987; 4,552,593; and 4,735,869. While glass has been mentioned as a possibility on many occasions, for instance in U.S. Pat. No. 3,331,699, commercial pearlescent products made using glass have been primarily for cosmetic applications in which relatively large glass platelet substrates have been coated.

Aforementioned U.S. Pat. No. 3,331,699 discloses that glass flakes may be coated with a translucent layer of particles of a metal oxide having a high index of refraction, such as titanium dioxide, provided there is first deposited on the glass flakes a nucleating substance which is insoluble in the acidic solution from which the translucent layer of metal oxide is deposited. The glass flakes as disclosed therein are on order of 1.0 to 5.0 microns in thickness, and varying in the size of the major dimension from about 10 microns to about 400 microns, with at least 50 percent below 75 microns and about 85 percent below 150 microns. An example from this patent sets forth the following glass flake size distribution.

| Sieve | Size in Microns | Wt. Percent |
| --- | --- | --- |
| 40 to 100 mesh | 149–420 microns | 12.9 |
| 100 to 200 mesh | 74–149 microns | 32.5 |
| 200 to 325 mesh | 44–74 microns | 22.0 |
| 325 to 400 mesh | 37–44 microns | 9.6 |
| Through 400 mesh | Less than 37 microns | 23.0 |

U.S. Pat. No. 5,436,077 teaches a glass flake substrate which has a metal covering layer on which is formed a dense protective covering layer of a metal oxide such as a titanium dioxide. In this patent, the nature of the glass is unimportant as the metallic coating provides the desired appearance and the overcoating of the metal oxide is present to protect the metallic layer from corrosive environments. Examples of a glass flake having an average diameter of 15 microns being plated with silver and then coated with a $SiO_2$ layer are disclosed.

In commonly assigned U.S. Pat. 6,045,914, there is disclosed a method for preparing smooth, uniform coatings of metal oxides on glass flakes which adhere to the glass flakes to yield high quality pearlescent pigments. In accordance with the method disclosed therein, a pearlescent pigment is formed by establishing a hydrous film layer of titanium and/or iron oxides on glass flakes and thereafter calcining the coated flakes provided that the glass flakes employed are C glass flakes and when the hydrous layer is titanium, the procedure is a rutilizing procedure. The glass flakes are disclosed as having have a size and shape mimicking the mica platelets used in the $TiO_2$ and $Fe_2O_3$-coated mica pearlescent pigments and thus have an average particle size in the range of about 1 to 250 microns and a thickness of about 0.1-10 microns. More cubic flakes having similar particle sizes and thickness of about 10-100 microns can be utilized, however, the pearlescent effect is significantly diminished due to the low aspect ratio. In all of the examples, however, pigments were made from glass flakes having an average diameter of 100 microns or more. The entire content of U.S. Pat. No. 6,045,914 is herein incorporated by reference.

The manufacture of synthetic platelets such as glass flakes often results in a size distribution of the platelets that can be characterized by Gaussian curves. A particularly useful means of characterizing the size distribution of a mass of synthetic platelets produced and used as substrates for effect pigments is by specifying the platelet size of the lowest 10 vol. %, 50 vol. %, and 90 vol. % of platelets along the Gaussian curve. This classification can be characterized as the D10, D50, and D90 values of the platelet size distribution. Thus, a substrate having a D10 of a certain size means that 10 vol. % of the flake substrate particles has a size up to that value. For example, the present assignee has numerous mica-based effect pigments on the market, in particular used for cosmetics and automotive paint applications. Among these is the LUMINA® mica-based pigment, which has a D10 of 10 microns, a D50 of 22 microns and a D90 of 45 microns. Thus, the size distribution of the LUMINA® mica-based pigment can be described as follows: 10 volume % of the mica platelets have a size of up to and including 10 microns, 50 volume % of the platelets have a size up to and including 22 microns, and 90 volume % of the platelets have a size up to and including 45 microns.

Glass flake-based effect pigments, however, as previously stated, have a substantially larger size. This is reflected in the size distribution. Thus, the present assignee and Nippon Sheet Glass market glass flake-based pigments under the tradenames REFLECKS™ and FIREMIST® based pigments, which have a D10 of 17 microns and D50 of 45 microns for the former and a D10 of 50 microns and D50 of 100 microns for the latter. These pigments are of a particular large size and cannot be effectively used for automotive paints inasmuch as the pigments themselves often protrude from the applied thin paint film adversely affecting the optical properties of the film. Moreover, the large pigments cannot readily pass through the spray apparatus often used to apply the paint. Other glass-based pigments such as a pigment commercialized by Merck under the tradename RONASTAR® are also of a large size, having D10s above 30 and D50s above 65.

In an attempt to manufacture an effect pigment from glass flake that will find acceptance in automotive paints, Nippon Sheet Glass has developed a glass flake substrate having a significantly smaller size distribution than previously formed. This product has a D10 of 8 microns, a D50 of 20 microns and a D90 of 37 microns. Application of $TiO_2$ coatings to produce an effect pigment for automotive paints, however, have not proven successful as the optical properties of the paint films formed from the pigments have lacked luster, depth, and sparkle.

SUMMARY

In accordance with the present invention, an effect pigment comprising a synthetic platelet substrate having coated thereon a translucent metal oxide coating is provided from a platelet substrate having a particular size distribution characterized as having a D10 of at least 9.5 microns, a D50 of between about 20 microns to less than 40 microns, and a D90 of over 35 microns to less than 85 microns.

The effect pigments produced from a coated synthetic platelet substrate having the desired size distribution have been found useful in all types of compositions, including plastics, cosmetics, and, in particular, automotive paints, without the prior art problems of plugging spray paint equipment and without the adverse protrusion of large platelets from the paint film that has plagued prior art effect pigments formed from synthetic platelets. On the other hand, the amount of small particles is minimized to reduce the light scattering effect of the smallest sized particles.

Surprisingly, it has been found that by increasing the D10 from 8 microns to at least 9.5 microns, a significant improvement in sparkle of a film formed from the pigment is achieved. The improved sparkle is found in a higher level of gloss and reflectivity of the film that is visibly noticeable.

DETAILED DESCRIPTION

In accordance with the present invention, a pearlescent pigment is formed by establishing a hydrous film layer of a metal oxide on a synthetic platelet substrate and thereafter calcining the coated platelets. The invention is particularly concerned with forming a pearlescent pigment from synthetic platelet substrates, which have a particular size distribution so as to enable the formed pigment to be used in a wide variety of products such as coloring plastics, cosmetics, and, in particular, for use in automotive paints. The synthetic platelet substrates for use in forming the pearlescent pigments of the present invention include, for example, aluminum oxide, silicon dioxide, bismuth oxychloride, boron nitride, and glass. Glass flake is of particular interest in the present invention.

The synthetic platelet substrates, such as glass flake substrate, used for the purposes of this invention are particles, for example, of glass, which have two dimensions (length and width) of similar magnitude and characteristically much greater than the third dimension. The platelets of this invention, which are useful as substrates for the application of the metal oxide coating, will have a size distribution characterized substantially by a Gaussian distribution in which the volume size fractions are distributed as follows: D10 is at least 9.5 microns, D50 from between about 20 to less than 40 microns, and a D90 of from over 35 to less than 85 microns. What the size distribution means is that at least 10 vol. % of the platelets will have a size up to and including at least 9.5 microns, at least 50 vol. % of the glass platelets will have a size of up to and including 20 to less than 40 microns, and at least 90 vol. % of the glass platelets will have a size up to and including 35 to less than 85 microns. It has been found that by shifting the D10 from 8 to at least 9.5 microns, the resulting pigments have less fines which scatter the light and negatively impact the sparkle of the films formed with the pigment. In general, the size distribution will follow a Gaussian distribution with the particles typically ranging in size from about 1 to about 150 microns in the largest dimension. Typically, the thicknesses of the synthetic platelets, including glass flakes, will range from about 0.1 to under 5 microns. The desired size and size distribution can be obtained by suitable classification of the flakes, such as by classifying through selected screens and the like.

Although the invention is directed to any type of synthetic platelet, glass flakes are particularly useful. The nature of the glass is not critical. For many purposes, clear, colorless glass flakes are desired, but it is also possible to use specialty glasses which may include glass in which a color has been imparted by the inclusion of selected chemicals in the melt.

Glass flakes are desirable in the industry because they are very resilient and can be optically attractive as well. The glass is primarily composed of $SiO_2$ and $Al_2O_3$ and can also include ZnO, CaO, $B_2O_3$, $Na_2O$ and $K_2O$ as well as FeO and $Fe_2O_3$. The glass flakes are made by stretching a molten glass into thin sheets, beads or glass tubes followed by crushing the glass into flakes. Large hollow spheres can be produced followed by solidification and crushing as well as a variety of other flake production methods. Glass can be classified as A glass, C glass or E glass. The A glass is a soda-lime glass and is commonly used to make windows. It contains more sodium than potassium and also contains calcium oxide. C glass, also known as chemical glass, is a form of glass which is resistant to corrosion by acid and moisture. It often contains zinc oxide as well as other oxides which makes the flakes more resistant to chemical destruction. E glass or electrical glass is, as the name implies, designed for electronic applications and although it is very stable at high temperatures, it can be susceptible to chemical attack. Table 1 following shows the composition of several commercial samples of A, C and E glasses in weight percent. It is recognized that C glass as well as A and E glass have broad windows regarding their chemical composition and in fact A and E glass compositions can be made very similar to C glass.

TABLE 1

| | Type | | | | |
|---|---|---|---|---|---|
| | A Glass | C Glass | C Glass | E Glass | E Glass |
| $SiO_2$ | 72.5 | 65–70 | 65% | 52–56 | 52.5 |
| $Al_2O_3$ | 0.4 | 2–6 | 4% | 12–16 | 14.5 |
| CaO | 9.8 | 4–9 | 14% | 20–25 | 22.5 |

TABLE 1-continued

| | Type | | | | |
|---|---|---|---|---|---|
| | A Glass | C Glass | C Glass | E Glass | E Glass |
| MgO | 3.3 | 0–5 | 3% | 0–5 | 1.2 |
| $B_2O_3$ | 0.0 | 2–7 | 5.5% | 5–10 | 8.6 |
| $Na_2O + K_2O$ | 5.8 | 9–13 | 8.5% | <0.8 | <0.5 |
| ZnO | — | 1–6 | 0 | — | — |
| $FeO/Fe_2O_3$ | 0.2 | — | 0 | — | 0.2 |

In the practice of the present invention, the C or chemical type glass is preferred. While metal oxide coatings of an A or E glass can be prepared, the resulting pigments do not have the quality of the products as C glass and hence have limited commercial value. When $TiO_2$ coated products are prepared, anatase or rutile crystal modifications are possible. The highest quality and most stable pearlescent pigments are obtained when the $TiO_2$ is in the rutile form. Also the glass used can influence the crystal form of the titanium dioxide coating. For instance, when common E glass is used, the resulting crystal phase is primarily anatase. In order to obtain rutile, an additive must be used which can direct the $TiO_2$ to the rutile modification.

Useful rutile directors such as tin are disclosed in commonly assigned U.S. Pat. Nos. 4,038,099 and 5,433,779 incorporated herein by reference in their entireties. If the present synthetic platelet is to be coated with titanium dioxide and rutile titanium dioxide is desired, the rutile director is located adjacent to the titanium dioxide. Other layers may be present between the glass and rutile director/rutile titanium dioxide.

The material that forms the thin outer layer on the glass flakes and imparts to them the desired nacreous character and interference color is a selected translucent metal oxide compound of high refractive index. The translucent compounds of this layer may be colorless or colored and thereby contribute color both by means of light absorption from the inherently colored compound, and by interference colors from the thin transparent layer having a high index of refraction. The preferred translucent metal oxides applicable to this invention are titanium dioxide and iron oxide. However, other representative metal oxides that function in a like manner when used alone include the oxides of zirconium, chromium, nickel, cobalt, tin, and hydrous forms thereof.

The coating of the glass flakes with metal oxide generally follows procedures known in the art for the formation of metal oxide-coated mica.

In general, the procedure involves the dispersing of the glass flake particulate and combining that dispersion with a precursor that forms a hydrous titanium oxide or other metal oxide film coating on the flakes. For example, iron and zirconium oxide are useful coatings alone or in addition to the titanium oxide coatings.

In the coating process, the glass flakes are dispersed in water, which is preferably distilled. The concentration of the glass flake in water can vary from about 5% to 30% although the generally preferred concentration varies between about 10% to 20%.

After the glass is dispersed in the water and placed in an appropriate vessel, the appropriate titanium or other metal source materials are introduced. The pH of the resulting dispersion is maintained at an appropriate level during the addition of the titanium or other metal by use of a suitable base such as sodium hydroxide to cause precipitation of the hydrous titanium dioxide or hydrous metal oxide on the glass flakes. An aqueous acid such as hydrochloric acid can be used for adjusting the pH. The coated platelets can, if desired, be washed and dried before being calcined to the final pearlescent pigment.

The source of the titanium is preferably titanium tetrachloride although, similarly, other sources known in the art can be employed. The source of the iron is preferably ferric chloride although any other iron source known in the prior art can be employed. If desired, layers of titanium and iron can be deposited sequentially. The procedures are well known in the art. For example, referring again to aforementioned U.S. Pat. No. 3,331,699, the entire content of which is herein incorporated by reference, it has now been found that glass flakes may be coated with a translucent layer of particles of a metal oxide having a high index of refraction, such as zirconium dioxide, chromium oxide and the like, especially titanium dioxide or hydrated titanium dioxide and iron oxide, provided there is first deposited on the glass flakes a nucleating surface comprising a very finely divided metal oxide compound which is insoluble in the acidic solution from which the said translucent layer of metal oxide is to be deposited. The resulting products are nacreous flake pigments that exhibit a high degree of lustrous sparkle as well as brilliant colors that vary with the thickness of the translucent layer of the metal oxide.

In accordance with the method of U.S. Pat. No. 3,331,699, the nacreous flake pigments comprise three components: 1) a glass flake substrate, 2) an acid insoluble metal oxide compound deposit on the glass flakes which forms a nucleating surface thereon that is receptive to the deposition of a layer of translucent metal oxide particles, and 3) a thin, translucent layer of metal oxide of selected small particle size deposited on the acid insoluble metal oxide surface.

In any case, the treated glass flakes are then suspended in water to which is added a strongly acid solution of a titanium salt such as titanyl sulfate. The mixture is heated, causing the titanium salt to hydrolyze to hydrous titanium dioxide that immediately and selectively deposits on the treated glass flakes. The amount of hydrous titanium dioxide which is deposited on the flakes can be built up in proportion to the amount of titanium salt liquor which is added to the hydrolyzing slurry, as well as in proportion to the time of heating. As this process proceeds, it is possible to follow the increasing thickness of the outer translucent layer of hydrous titanium dioxide by observing the change in the interference colors from an initial silver appearance to gold, and progressively to red, violet, blue, and green. By the proper selection of the amount of titanium salt used, any desired interference color can be readily achieved.

The optical principles which explain interference colors are well known and are discussed in many textbooks of physical optics such as Robert W. Wood's "Physical Optics," third edition, New York, 1936, page 198. Briefly stated, interference is an optical phenomena associated with the reflectance of light from the surfaces of thin films, wherein there is a reduction in the intensity of a certain wave length of the incident light (restructive interference) and reinforcement of other wave lengths (constructive interference). The extent to which particular wave lengths are affected is dependent upon the thickness of the film and its refractive index. When the thickness is such that a ray reflected from one surface of a film is out of phase with a ray which has passed through the film and been reflected from the other surface, there is destructive interference.

Since there is a phase reversal when light is reflected from the surface of a medium of higher refractive index, the condition of maximum destructive interference (minimum reflectance) is satisfied when the effective optical path (twice the thickness multiplied by refractive index) in a film of high refractive index is one wave length or a simple multiple thereof. Considering the refractive index, N, of the film, the thickness (t) thereof for destructive interference with any wave length A is given by the formula:

$$t = n\lambda/2N$$

where n is a small whole number usually not greater than 5.

By the same line of reasoning, if the two rays emerge in phase, there is reinforcement or a maximum of reflectance. This condition is satisfied, again assuming phase reversal, when the effective optical path is one-half a wave length or an odd multiple thereof, the formula for the thickness at maximum reflectance being:

$$t = (n+\tfrac{1}{2})\lambda/2N$$

where n is 0 or a small whole number usually not greater than about 5.

When n is greater than 1, it is common to speak of the interference as a higher order, second order, third order, and the like.

From the above, it can be seen that the nacreous pigment compositions of the invention are prepared by slurrying glass flakes in an aqueous medium with a colloidal suspension of a suitable metal oxide compound, whereupon said metal oxide compound is deposited on the glass flakes as a nucleating surface and rendered insoluble in the acidic solution from which the translucent layer of metal oxide will be deposited. The metal oxide on the glass flakes is insolubilized by heating and/or stirring the aqueous medium containing the glass flakes. The treated glass flakes are then receptive to the deposition of an outer layer of a translucent metal oxide having a high refractive index from a salt solution of a metal such as, for example, titanium, zirconium, chromium, iron, nickel, tin, or cobalt.

The amount of the metal oxide compound required to be deposited as a nucleating surface seems to be somewhat critical for optimum results, although the optimum amount to use seems to vary for the different useful agents. The minimum useful amount of metal oxide compounds appears to be at least about 0.2% metal oxide compound based on the weight of the glass flakes. Using tin oxide, the preferred amount is in the range of 0.5% to 2% but much larger amounts may be used, up to 35% or even 50% by weight, with some sacrifice in quality at the higher level. Using hydrous $TiO_2$ as the nucleating surface, the optimum amounts seems to lie in the lower part of the range, say 0.4% to 1%, preferably 0.4% to 0.5% by weight. Optimum amounts of fibrous alumina are also in the lower part of the range, for example 1% to 5% by weight.

For most purposes, the preferred and most versatile metal oxide compound to form the nucleating surface is a tin oxide compound. For convenience, it is considered as stannic oxide ($SnO_2$), but its exact nature is not known, hence the designation "tin oxide compound." It is probably first precipitated as a hydrous oxy-salt (oxy-chloride, for instance) and largely converted to the oxide during the insolubilization step. Various tin salts may be used as the source of the tin oxide compound and both stannous and stannic salts are applicable. It is characteristic of many tin salts that the solutions readily hydrolyze on dilution to form highly colloidal suspensions which are positively charged. This pronounced tendency to form colloidal suspensions appears to be the property which makes tin compounds so versatile in the proposed use. Insolubilization of the nucleating surface of tin oxide compound is readily effected by the heat, either by drying the isolated flakes or by heating the slurry to relatively high temperatures.

The successful deposit of a nucleating surface of hydrous titanium dioxide or hydrous zirconium dioxide requires special care because the formation of colloidal suspensions of these compounds is not as readily achieved as it is with tin compounds. However, techniques of preparing colloidal suspensions of such hydrous metal oxides are well known. For instance, if a precipitated hydrous titanium dioxide is washed free of soluble salts, and any residual acid finally neutralized, the resulting paste is readily peptized to a colloidal suspension by adding a small amount of hydrochloric acid. A similar technique may be used to prepare a colloidal suspension of hydrous zirconium dioxide, except that acetic acid is preferred as the peptizing acid. Exposure of the glass flakes to such a colloid followed by a heat treatment for insolubilization gives an effective nucleating surface. It is also possible to form the colloidal suspension in the presence of the glass flakes, with almost instantaneous deposition of the nucleating surface, by slurrying the flakes in a very dilute solution of titanyl suflate (in the order of 0.1% concentration based on $TiO_2$ content) followed by slow heating to near the boil. A nucleating surface of hydrous zirconium oxide may also be deposited in a similar fashion. In using fibrous boehmite as the nucleating surface, it is necessary first to disperse it in a colloidal form by vigorous agitation in water after which the glass flakes are slurried in this colloidal suspension, separated from the water, and dried at a temperature of 80° C. or above. This form of alumina, known as fibrous boehmite, is quite unique in its ability to form a positively charged colloidal suspension which can be converted to an acid insoluble form, in comparison to the usual form of alumina-hydrate that has not been converted to the fibrous boehmite form and does not readily become insoluble in dilute acid.

The amount of titanium salt used in relation to the treated glass flakes may vary over a wide range and is significant only as a control on the thickness of the ultimate oxide coating. In general, the usage calculated as $TiO_2$ may be in the range of about 4 parts per 100 parts of glass flakes up to as much as about 40 parts per 100 parts of glass flakes, with a preferred range for $TiO_2$ of about 4 to 20 parts per 100 parts of glass flakes. The usage of the $TiO_2$ is, of course, reflected in the thickness of the layer deposited and the resulting interference color. Table 2 following sets forth the analysis of a series of samples for $TiO_2$ and it is quite evident there is correlation between the amount of $TiO_2$ actually deposited on the glass flakes and the resulting interference colors.

TABLE 2

| Color | Percent $TiO_2$ |
| --- | --- |
| Silver flakes | 3.0 |
| Gold flakes | 5.8 |
| Violet flakes | 7.4 |
| Blue flakes | 8.6 |

It has been found that the outer translucent layer may vary in thickness from a range of about 20 nanometers to about 250 nanometers in order to produce products that vary in color as the thickness of the layer is increased.

An exterior treatment may be desired on the present effect pigment. Examples of useful exterior treatments are disclosed in commonly assigned U.S. Pat. Nos. 5,156,889; 5,423,912; and 5,759,255 incorporated herein by reference in their entireties.

Products of this invention have use in all types of automotive paint applications. For example, these effect pigments can be used in mass tone or as styling agents to spray paint all types of automotive and non-automotive vehicles. Similarly, they can be used on all clay/formica/wood/glass/metal/enamel/ceramic and non-porous or porous surfaces. The effect pigments can be used in coating compositions or incorporated into plastic articles geared for the toy industry or the home. These effect pigments can be impregnated into fibers to impart new and esthetic coloring to clothes and carpeting. They can be used to improve the look of shoes, rubber and vinyl/marble flooring, vinyl siding, and all other vinyl products. In addition, these colors can be used in all types of modeling hobbies. Natural Pearl Pigments have limited industrial applications, again due to temperature, pH, shear, cost and an inability to achieve high total solids content without destroying crystalline structure.

The above-mentioned compositions in which the compositions of this invention are useful are well known to those of ordinary skill in the art. Examples include printing inks, nail enamels, lacquers, thermoplastic and thermosetting materials, natural resins, and synthetic resins. Some non-limiting examples include polystyrene and its mixed polymers, polyolefins, in particular, polyethylene and polypropylene, polyacrylic compounds, polyvinyl compounds, for example polyvinyl chloride and polyvinyl acetate, polyesters and rubber, and also filaments made of viscose and cellulose ethers, cellulose esters, polyamides, polyurethanes, polyesters, for example polyglycol terephthalates, and polyacrylonitrile.

For a well-rounded introduction to a variety of pigment applications, see Temple C. Patton, editor, The Pigment Handbook, volume II, Applications and Markets, John Wily and Sons, New York (1973). In addition, see for example, with regard to ink: R. H. Leach, editor, The Printing Ink Manual, Fourth Edition, Van Nostrand Reinhold (International) Co. Ltd., London (1988), particularly pages 282-591; with regard to paints: C. H. Hare, Protective Coatings, Technology Publishing Co., Pittsburgh (1994), particularly pages 63-288. The foregoing references are hereby incorporated by reference herein for their teachings of ink, paint, and plastic compositions, formulations and vehicles in which the compositions of this invention may be used including amounts of colorants.

In the cosmetic field, the effect materials can be used in all cosmetic and personal care applications subject, of course, to all regulatory requirements. Thus, they can be used in hair sprays, leg-makeup, insect repellant lotion, mascara cake/cream, nail enamel, nail enamel remover, perfume lotion, and shampoos of all types (gel or liquid). In addition, they can be used in shaving cream (concentrate for aerosol, brushless, lathering), skin glosser stick, skin makeup, hair groom, eye shadow (liquid, pomade, stick, pressed, or cream), eye liner, cologne stick, cologne, cologne emollient, bubble bath, body lotion (moisturizing, cleansing, analgesic, astringent), after shave lotion, after bath milk, and sunscreen lotion.

For a review of cosmetic applications, see Cosmetics: Science and Technology, $2^{nd}$ Ed., Eds: M. S. Balsam and Edward Sagarin, Wiley-Interscience (1972) and deNavarre, The Chemistry and Science of Cosmetics, $2^{nd}$ Ed., Vols 1 and 2 (1962), Van Nostrand Co Inc., Vols 3 and 4 (1975), Continental Press, both of which are hereby incorporated by reference.

In order to further illustrate the invention, various non-limiting examples are set forth below. In these, as well as throughout the balance of this specification and claims, all parts and percentages are by weight and all temperatures are in degrees centigrade unless otherwise indicated.

What is claimed is:

1. An effect pigment comprising a synthetic platelet coated with a translucent metal oxide film, said synthetic platelet having a size distribution characterized as a D10 of at least 9.5 microns, a D50 of between about 20 and less than 40 microns, and a D90 of over 35 to less than 85 microns.

2. The effect pigment of claim 1 wherein said size distribution is a substantially Gaussian distribution.

3. The effect pigment of claim 1 wherein said synthetic platelet substrate comprises glass flakes.

4. The effect pigment of claim 1 wherein said metal oxide film comprises titanium dioxide.

5. The effect pigment of claim 1 wherein said metal oxide film comprises iron oxide.

6. The effect pigment of claim 3 wherein said metal oxide film comprises titanium dioxide.

7. The effect pigment of claim 3 wherein said metal oxide film comprises iron oxide.

8. The effect pigment of claim 1 having a D10 of about 9.5 microns, a D50 of about 22 microns, and a D90 of about 45 microns.

9. The effect pigment of claim 1 wherein said synthetic platelet is selected from aluminum oxide, silicon dioxide, bismuth oxychloride, boron nitride, and glass.

10. The effect pigment of claim 9 wherein said metal oxide is titanium dioxide, iron oxide, zirconium oxide, chromium oxide, nickel oxide, cobalt oxide, tin oxide, or combinations thereof.

11. The effect pigment of claim 4 comprising from about 2.5 to 10% by weight $TiO_2$.

12. The effect pigment of claim 11 wherein said synthetic platelet is glass flake.

13. A plastic colored with the effect pigment of claim 1.

14. A cosmetic colored with the effect pigment of claim 1.

15. A paint suitable for automobiles colored with the effect pigment of claim 1.

16. The paint of claim 15 wherein said metal oxide is selected from the oxides of titanium, iron, or mixtures thereof.

17. The paint of claim 15 wherein said synthetic platelet is glass flake.

18. The paint of claim 15 wherein the size distribution of said synthetic platelet comprises a D10 of about 9.5 microns, a D50 of about 22 microns, and a D90 of about 45 microns.

19. The paint of claim 17 wherein said metal oxide is selected from the oxides of titanium and/or iron.

20. The paint of claim 15 wherein said platelet substrate is selected from aluminum oxide, silicon dioxide, bismuth oxychloride, boron nitride, and glass.

* * * * *